United States Patent
Mashak (10) Patent No.: US 10,709,857 B2
(45) Date of Patent: Jul. 14, 2020

(54) MANUAL VENTILATION METHOD AND SYSTEM

(71) Applicant: General Electric Company, Schenectady, NY (US)

(72) Inventor: James Nyal Mashak, Sun Prairie, WI (US)

(73) Assignee: General Electric Company, Schenectady, NY (US)

(*) Notice: Subject to any disclaimer, the term of this patent is extended or adjusted under 35 U.S.C. 154(b) by 285 days.

(21) Appl. No.: 15/836,307

(22) Filed: Dec. 8, 2017

(65) Prior Publication Data

US 2019/0175855 A1    Jun. 13, 2019

(51) Int. Cl.
*A61M 16/00*    (2006.01)
*A61M 16/20*    (2006.01)
(Continued)

(52) U.S. Cl.
CPC ...... *A61M 16/022* (2017.08); *A61M 16/0003* (2014.02); *A61M 16/0078* (2013.01);
(Continued)

(58) Field of Classification Search
CPC ...... A61M 16/0003; A61M 2016/0027; A61M 16/0045; A61M 16/0078; A61M 16/0081; A61M 16/01; A61M 16/021; A61M 16/022; A61M 16/024; A61M 16/0891; A61M 16/104; A61M 16/12; A61M 16/204; A61M 16/22; A61M 2202/0241; A61M 2202/0283; A61M 2205/07;
(Continued)

(56) References Cited

U.S. PATENT DOCUMENTS 4,550,726 A * 11/1985 McEwen ........... A61M 16/0051
                                                    128/202.22
5,497,767 A    3/1996 Olsson et al.
(Continued)

FOREIGN PATENT DOCUMENTS

EP    2371410    10/2016

OTHER PUBLICATIONS

International Search Report and Written Opinion of the International Searching Authority; dated Mar. 28, 2019; 11 pages.

*Primary Examiner* — Samchuan C Yao
*Assistant Examiner* — Danielle Roman
(74) *Attorney, Agent, or Firm* — Andrus Intellectual Property Law, LLP (57) ABSTRACT

A manual patient ventilation system includes a breathing bag manually compressed by a clinician to ventilate a patient via a patient interface device, a gas supply system supplying fresh gas to the breathing bag at a fresh gas flow rate, a pressure sensor measuring a patient airway pressure (PAW) throughout a compression and release cycle of the breathing bag by the clinician, a fresh gas controller comprising a processor, and a manual ventilation control module executable on the processor by the fresh gas controller. The manual ventilation control module includes instructions executable to receive the Paw measurements and determine a fresh gas flow rate based thereon. The gas supply system is then controlled to supply the fresh gas flow rate into the breathing circuit.

19 Claims, 5 Drawing Sheets

(51) Int. Cl.
*A61M 16/10* (2006.01)
*A61M 16/01* (2006.01)
*A61M 16/08* (2006.01)
*A61M 16/22* (2006.01)

(52) U.S. Cl.
CPC .......... *A61M 16/01* (2013.01); *A61M 16/024* (2017.08); *A61M 16/0891* (2014.02); *A61M 16/104* (2013.01); *A61M 16/202* (2014.02); *A61M 16/204* (2014.02); *A61M 16/208* (2013.01); *A61M 16/0081* (2014.02); *A61M 16/209* (2014.02); *A61M 16/22* (2013.01); *A61M 2016/0027* (2013.01); *A61M 2016/0039* (2013.01); *A61M 2205/3334* (2013.01); *A61M 2205/502* (2013.01)

(58) Field of Classification Search
CPC ........ A61M 2205/071; A61M 2205/33; A61M 2205/3331; A61M 2205/3334; A61M 2205/3342; A61M 2205/3344; A61M 2206/00; A61M 2206/20; A61M 2230/005; A61M 2230/40; A61M 2016/0039; A61B 5/097

See application file for complete search history.

(56) References Cited

U.S. PATENT DOCUMENTS

| | | |
|---|---|---|
| 2001/0022179 A1 | 9/2001 | Kitten |
| 2007/0125377 A1 | 6/2007 | Heinonen |
| 2009/0277448 A1 | 11/2009 | Ahlmén |
| 2011/0315139 A1* | 12/2011 | Mashak ................ A61M 16/01 128/203.14 |
| 2012/0272960 A1 | 11/2012 | Milne |
| 2015/0114396 A1* | 4/2015 | Ramanan ............ A61M 16/024 128/204.23 |

* cited by examiner

MANUAL VENTILATION METHOD AND SYSTEM

BACKGROUND

The present disclosure generally relates to ventilator systems and methods of control therefor, and more particularly to manual ventilation systems and methods providing fresh gas flow into the manual ventilation circuit.

Anesthesia machines are optimized for delivering anesthesia to a patient using volatile anesthetic agent liquids. In such systems, the anesthetic agent is vaporized and mixed into the breathing gas stream in a controlled manner to provide a gas mixture for anesthetizing the patient for a surgical operation. The most common volatile anesthetic agents are halogenated hydrocarbon chains, such as halothane, Enflurane, Isoflurane, Sevoflurane and Desflurane. Additionally, nitrous oxide ($N_2O$) can be counted in this group of volatile anesthetic agents, although the high vapor pressure of nitrous oxide causes nitrous oxide to vaporize spontaneously in the high pressure gas cylinder, where it can be directly mixed with oxygen. The anesthetizing potency of nitrous oxide is seldom enough to anesthetize a patient and therefore is typically mixed with one or more other volatile agents.

Anesthesia machines designed to deliver volatile anesthetic agents are designed to provide oxygen to the patient and eliminate carbon dioxide, while preserving the anesthetic gases. These goals are typically met using a re-breathing circuit, where an exhaled gas is cleaned to remove carbon dioxide and then re-introduced into the inhalation limb leading to the patient. In such a re-breathing circuit, carbon dioxide is absorbed from the expired gases by a carbon dioxide absorber. Before inhalation by the patient, the inhalation gas is supplied with additional fresh gas, such as air and/or oxygen mixed with vaporized aesthetic agents.

In addition to mechanical ventilation provided by the anesthesia machine, anesthesia ventilation involves ability for the clinician to manually ventilate the patient. Manual ventilation is typically provided by the clinician squeezing and releasing a breathing bag which then forces circulation of gasses through the re-breathing circuit. This functionality is often utilized during an anesthesia induction and when weaning the patient from the anesthesia and ventilator to provide assistance with spontaneous breathing and lung recruitment. A desired property of manual ventilation system is given haptic feedback of the patient breath volume. Such feedback is achieved when the patient exhalation volume is collected to the manual breathing bag.

The currently most used arrangement in ventilating manually is to have a breathing system equipped with an APL (Airway Pressure Limiting) valve. The APL valve is set by the clinician to an APL setting—a pressure setting at which the valve opens to let gas escape from the re-breathing circuit. When the manual ventilation bag is squeezed the gas volume is initially delivered to the patient, but when the APL pressure limit is reached the valve starts to bleed gas out from the circuit. The valve will form a resistance and as the bag is further squeezed some of the volume will go to the patient and some will bleed through the valve.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of controlling fresh gas flow during manual ventilation by a clinician includes measuring a patient airway pressure (Paw) of a patient throughout a compression and release cycle of a breathing bag by a clinician, wherein the Paw is measured with a pressure sensor in a breathing circuit ventilating the patient. A measured minimum Paw is determined during a release stroke of the compression and release cycle, and is compared to a desired minimum Paw to determine a difference therefrom. A fresh gas flow rate of fresh gas into the breathing circuit is calculated based on the Paw and the difference between the measured minimum Paw and the desired minimum Paw, wherein the fresh gas flow rate may be a constant flow rate or a flow rate pattern that changes over the compression release cycle. A gas supply system is controlled accordingly to supply the fresh gas flow rate for at least a portion of the compression and release cycle.

In one embodiment, a manual patient ventilation system includes a breathing bag manually compressed by a clinician to ventilate a patient via a patient interface device, a gas supply system supplying fresh gas to the breathing bag at a fresh gas flow rate, a pressure sensor measuring a Paw throughout a compression and release cycle of the breathing bag by the clinician, a fresh gas controller comprising a processor, and a manual ventilation control module executable on the processor by the fresh gas controller. The manual ventilation control module includes instructions executable to receive the Paw measurements and determine a fresh gas flow rate based thereon. The gas supply system is then controlled to supply the fresh gas flow rate into the breathing circuit.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their experience, experimentation, and research in the relevant field, the present inventor has recognized that one problem with current manual ventilation systems providing fresh gas flow into a re-breathing ventilation circuit is that the fresh gas is provided at a constant rate, regardless of pressure in the ventilation circuit and/or the ventilation state of the patient. Variation automatically occurs in manual ventilation due to the fact that ventilation flow and pressure is based on manual input from the clinician—i.e., the clinician's manual compression and release of the breathing bag. Furthermore, pressure changes in the system result from the release of gas by the APL valve, where a varying amount of gas will be released out of the system depending on how much the APL setting is exceeded and for how long during a compression stroke of the breathing bag by the clinician. Thus, pressure cycles within current manual ventilation circuits often fluctuate and are difficult to control, requiring significant manual intervention and pressure regulation by the clinician. For example, the clinician must bleed gas out of the system when the residual pressure within the system starts to become too high. Clinicians may vent pressure from the system by, for example, gapping the mask from the patient's face to allow gas to escape or by manually opening a valve to allow gas to escape. For example, the clinician may compress the breathing bag to reach the APL valve setting so as to release gas through the APL valve, provided that the APL valve is set appropriately. In certain examples, the clinician may temporarily reduce the APL setting below the current pressure in the circuit in order to open the APL valve and vent gas there through, and then return the APL valve to the normal APL setting once the pressure is sufficiently reduced. Alternatively or additionally, clinicians may manually adjust the fresh gas flow rate into the system.

Further, the inventor has recognized that it would be desirable to enable delivery of Positive End Expiratory Pressure (PEEP) to a patient during manual ventilation, which is not possible in current manual ventilation circuits because sufficient pressure control is not possible.

In view of the foregoing challenges and shortcomings of prior art systems, the inventor developed the disclosed system that adjusts the fresh gas flow rate into the manual ventilation system based on a measured patient airway pressure (Paw). In a system with automated electronic fresh gas control provided by a fresh gas controller, the controller receives Paw measurements from a pressure sensor positioned to measure patient airway pressure, and automatically calculates and implements a fresh gas flow rate in order to maintain a desired minimum Paw during the expiration portion of the breathing cycle. The fresh gas flow rate may be a steady, constant flow rate for some or all of the compression release cycle, or a varying flow rate throughout the compression and release cycle. Thereby, the disclosed system and method enable the provision and automatic maintenance of PEEP, which is desirable and provides superior ventilation for certain patients.

Furthermore, the disclosed method and system automatically provide more consistent ventilation to the patient by synchronizing the fresh gas flow rate with the compression activity by the clinician. In certain embodiments, the fresh gas controller may be further configured to learn a clinician's compression pattern and to automatically compensate for expected losses of gas through the APL valve. In such embodiments, the system automatically adjusts for changes in the clinician's activity as compared to the expected compression pattern from the clinician, to thereby account for the irregularities of human control. Namely, the inventor has recognized that clinicians generally fall into a particular compression and release pattern, including a patterned compression force and a rate of change of pressure resulting from the clinician's compression force pattern on the breathing bag. However, the inventor has further recognized that such patterns, although frequent, are not always repeated for all compression strokes by a clinician, and that different clinicians may provide differing compression and release patterns. Moreover, some clinicians may not apply a consistent pattern at all, and thus pressure regulation may require ongoing automatic adjustment of the fresh gas flow rate.

Figure 1:
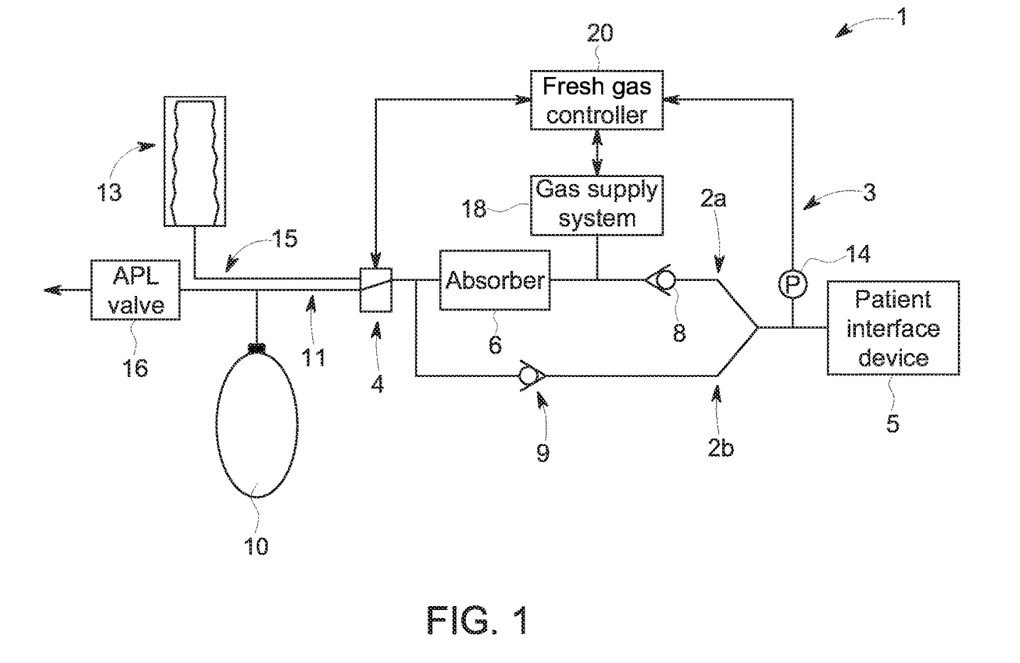
FIG. 1 is a schematic diagram of an exemplary patient ventilation system providing manual patient ventilation.

FIG. 1 is a schematic diagram depicting one embodiment of a ventilation system 1 configured to provide a manual breathing circuit. A looped breathing circuit 3 is formed by an inhalation branch 2a bringing ventilation gases to a patient, and an exhalation branch 2b delivering exhaled gases from the patient back into the system. The breathing circuit connects to the patient at a patient interface device 5, which may be any means of connecting to a patient's respiratory system in order to deliver and remove respiratory gasses therefrom. In exemplary embodiments, the patient interface device 5 may be a respiratory mask, an intubation tube, or other devices for sealably connecting to a patient's upper airways in order to provide a closed breathing circuit 3. The gasses exhaled by a patient are rich in carbon dioxide ($CO_2$), and contain anesthetic products. It is desirable to recover and recycle the breathing gasses, such as to maintain and reuse the anesthetic agent; however, recycling the exhaled gasses requires removal of the $CO_2$. Accordingly, the breathing circuit 3 includes an absorber 6 positioned therein to capture and remove the carbon dioxide therefrom. In the depicted embodiment, the absorber 6 is positioned within the inhalation branch 2a delivering gas to the patient via the patient interface device 5. However, in other embodiments the absorber 6 may be placed elsewhere within the circuit, such as in the exhalation branch 2b or in both the inhalation and exhalation branches.

The inhalation and exhalation branches 2a and 2b are equipped with an APL valve 16 that, as described above, opens at a certain pressure value in order to release excess gas and eliminate any overpressure during the inhalation cycle, as overpressure can be harmful to a patient. Additionally, the inhalation branch 2a and the exhalation branch 2b are equipped with non-return valves 8 and 9 that control the gas flow in the desired direction about the breathing circuit 3. To provide one example, the non-return valves 8 and 9 may be check valves arranged to only allow flow in one direction, towards the patient in the inhalation branch 2a and away from the patient in the exhalation branch 2b.

A manual breathing bag 10 is provided to allow the clinician to control gas flow through the breathing circuit 3. Namely, compression of the breathing bag 10 forces ventilation gasses to the patient through the inhalation branch 2a, and release of the breathing bag 10 allows the breathing bag to fill as the contraction of the patient's chest and lungs forces gasses exhaled from a patient toward the breathing bag 10 through the exhalation branch 2b. Thereby, the compression and release cycle of the breathing bag 10 controls ventilation of the patient, where the compression stroke provides a breath to the patient and the release stroke allows for exhalation of exhaled gasses away from the patient. The breathing bag is connected to the breathing circuit 3 via line 11. In the depicted example, the patient ventilation system 1 is in manual mode, where the switch 4 is arranged between the breathing bag 10 and the inhalation and exhalation branches 2a and 2b. The switch 4 is arranged to enable switching between the manual mode, where the breathing bag 10 and line 11 are connected, and a mechanical ventilation mode where a mechanical ventilator 13 is connected to the inhalation and exhalation branches 2a, 2b via line 15. Switching between the mechanical ventilation mode and the manual ventilation mode may be performed by any number of switches 4 and/or switch control means, including manually or electrically controlled mechanical switches.

The system further includes a fresh gas controller 20 controlling a gas supply system 18 supplying breathing gasses to the patient. The gas supply system 18 supplies fresh gas, which may include air, $O_2$, and/or volatile anesthetic agents. In the depicted embodiment, the gas supply system 18 is connected at the inhalation branch 2a upstream from the non-return valve 8. Thus, when the non-return valve 8 is closed during the exhalation portion of the breathing cycle, or the release stroke, the fresh gas supplied by the gas supply system 18 flows toward the breathing bag 10 to mix with the exhaled gas, which inflates the breathing bag 10. Pressure sensor 14 is positioned within the breathing circuit in order to measure the Paw. Pressure measurements from the pressure sensor 14 are provided to the fresh gas controller 20 which utilizes the pressure measurements in order to control the gas supply system 18 accordingly. In certain embodiments, the switch 4 may be controlled by the fresh gas controller 20, such as to switch into a manual ventilation mode. In other embodiments, a sensor within the switch 4 may provide information to the fresh gas controller 20 about its state. In other embodiments, the switch 4 may be a simple manual switch, with no electronic communication with the fresh gas controller 20. In such embodiments, the fresh gas controller 20 may receive information regarding a switch to manual mode from a clinician, such as via a user interface for the anesthesia system.

Figure 2:
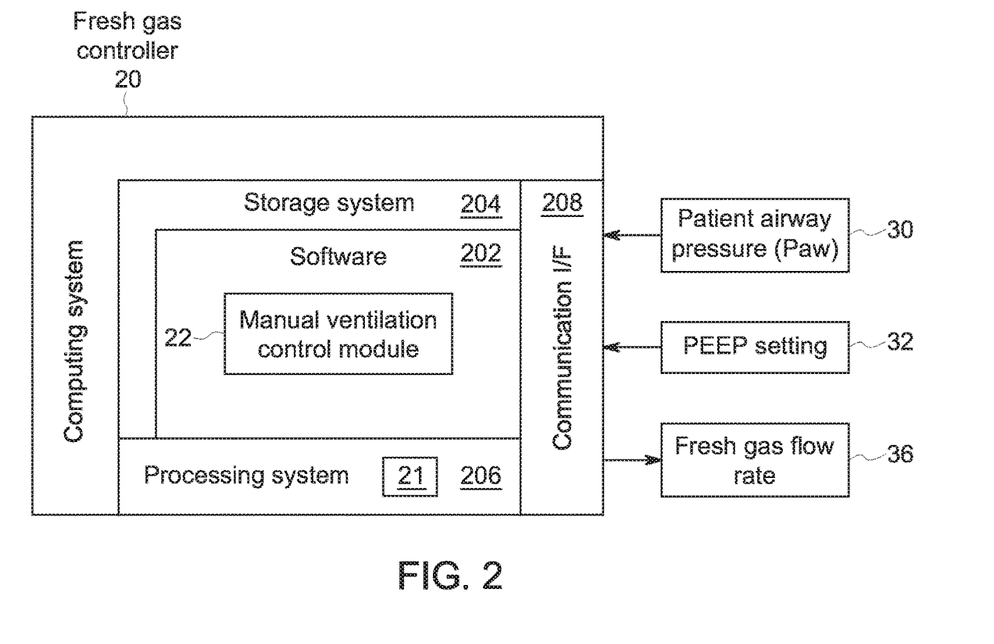
FIG. 2 is a schematic diagram of an exemplary fresh gas controller for controlling fresh gas flow into a manual ventilation circuit during manual ventilation by a clinician.

FIG. 2 is a schematic depiction of an exemplary fresh gas controller, which in the example comprises a processing system 206 including a processor 21 and storage system 204 having software 202 that includes a manual ventilation control module 22. The manual ventilation control module 22 comprises computer executable instructions that, when executed by the processing system 206, provide control instructions to the gas supply system 18 in order to control the flow rate of fresh gas into the manually-controlled breathing circuit 3. Specifically, the manual ventilation control module 22 is configured to receive the Paw measurements 30 measured by the pressure sensor 14 and to calculate a fresh gas flow rate 36 accordingly. In certain embodiments, the manual ventilation control module 22 may also receive a PEEP setting 32, such as a pressure value set by a user to limit the minimum pressure during the release stroke to the value of the PEEP setting 32.

Figure 3:
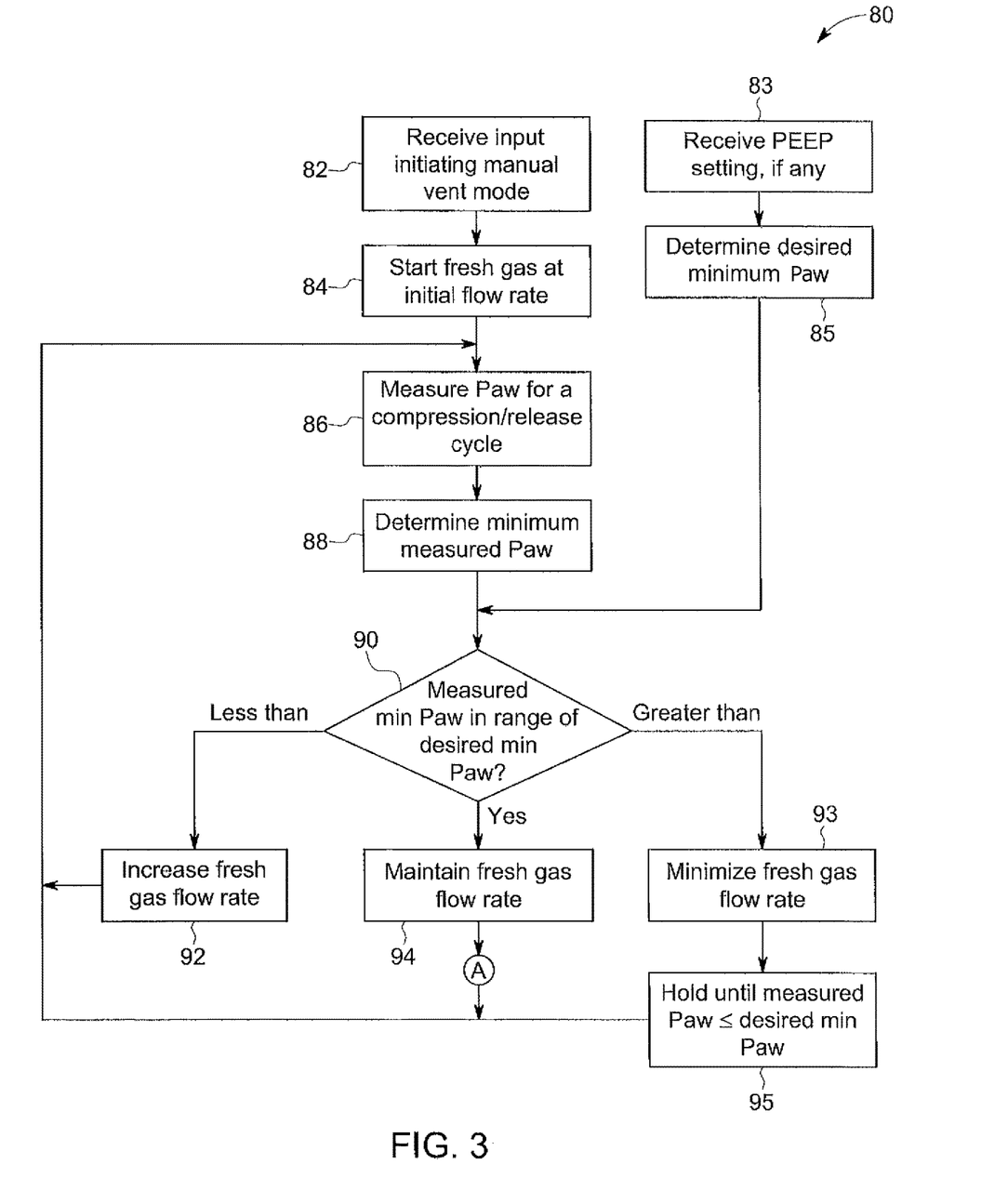
FIG. 3 is a flow chart depicting steps of an exemplary method of controlling fresh gas flow during manual ventilation.

FIG. 3 depicts one exemplary method 80, or portion thereof, of controlling fresh gas flow rate during manual ventilation being administered by a clinician. An input initiating ventilation mode is received at step 82. In various embodiments, the input could be from a clinician via the user interface, and/or input from the sensor in a switch 4 sensing the movement of the switch 4 into a position connecting the breathing bag 10 to the breathing circuit 3. A PEEP setting is also received at step 83, if any is provided by a clinician. In certain embodiments, the system 1 may be configured to provide a default desired minimum Paw, which may be, for example, atmospheric pressure or equivalent with the surrounding pressure. In embodiments where the system 1 is capable of providing PEEP, the PEEP setting 32 may be provided, for example, by the clinician via a user interface for the system 1. In examples where a PEEP setting 32 for the system 1 was already provided when operating in a mechanical ventilation mode, the same PEEP setting may automatically carry over and be utilized by the manual ventilation control module 22 in order to determine the fresh gas flow rate 36. If a PEEP setting 32 is provided, then the desired minimum Paw is determined at step 85 based on the PEEP setting 32. For example, the desired minimum Paw may be set to equal the PEEP setting value. In certain embodiments, a trigger pressure may also be determined, such as based on the PEEP setting 32 and/or the desired minimum Paw, which is explained in more detail with respect to FIG. 4.

Upon starting the manual ventilation mode, a fresh gas flow is started at step 84, which is provided at an initial flow rate. The initial flow rate may be a default setting, or may be based on patient information or operational history carried over from a mechanical ventilation control module. The Paw 30 is measured for at least one compression and release cycle at step 86. A minimum measured Paw is determined at step 88 based on the Paw measurements over the compression and release cycle. In certain embodiments, the Paw measurements may be filtered to remove noise, and the minimum measured Paw may be determined based on the filtered data. Alternatively or additionally, the minimum measured Paw may be determined as a mean or average of a predetermined number of pressure samples at the end of the release stroke RS, or expiration of the patient.

The measured minimum Paw represents the low point of the pressure in the patient's air way, which ideally is maintained at the desired minimum Paw (such as the PEEP setting). Step 90 is executed to determine whether the measured minimum Paw is approximately equal to the desired minimum Paw, such as whether the measured minimum Paw is within a predetermined range of the desired minimum Paw. If the measured minimum Paw is less than the desired minimum Paw by at least the predetermined amount, then the fresh gas flow rate 36 is increased at step 92. For example, the manual ventilation control module 22 may be configured to calculate the increase in fresh gas flow rate 36 by an amount proportional to the difference between the measured minimum Paw and the desired minimum Paw. In other embodiments, the fresh gas flow rate 36 may be increased by a predetermined amount. Either way, the fresh gas flow rate 36 may be increased incrementally to bring the measured minimum Paw up to the desired minimum Paw, such as the PEEP setting $P_1$, over several compression and release cycles without over pressurizing the breathing circuit.

If, on the other hand, the measured minimum Paw is greater than the desired minimum Paw by at least the predetermined amount, then step 93 is executed to immediately minimize the fresh gas flow rate 36. In that scenario, the residual pressure within the system is too high and gas needs to be removed so that full inhalation and exhalation cycles can be provided to the patient. As described above, such removal is performed by the clinician, such as by letting gas escape from the patient interface device 5 (e.g. gapping the breathing mask slightly away from the patient's face) or through a release valve (e.g., by compressing the breathing bag up to the APL valve setting to release gas through the APL valve and/or temporarily decreasing the APL setting of the APL valve 16 below the measured minimum Paw) to remove gas from the breathing circuit 3 and reduce the pressure therein. The minimized gas flow rate may be a set value that provides the minimum fresh gas necessary to deliver the needed gas to the patient, such as to deliver the needed amount of anesthetic agent. In certain embodiments, the minimum fresh gas flow rate may be zero, in other embodiments the minimum fresh gas flow rate may be greater than zero, but still a low value that does not materially affect the pressure within the breathing circuit 3. To provide just one example, the minimum fresh gas flow rate may be 1 liter/min. Such a minimum fresh gas flow rate could compensate for gas lost from the breathing circuit (e.g. not having a tight seal around the face mask), as well as provide at least some anesthetic agent into the breathing circuit. At step 95, the minimum fresh gas flow rate is maintained until the measured Paw is less than or equal to the desired minimum Paw, so as not to unnecessarily increase the pressure within the breathing circuit 3.

If, at step 90, the measured minimum Paw is within the predetermined range of the desired minimum Paw, then the fresh gas flow rate is maintained at step 94. In other words, the fresh gas flow rate provided for the most recent Paw cycle where the measured minimum Paw was approximately equal to the desired minimum Paw is maintained for a subsequent compression and release cycle. The method then returns to step 86, where the Paw is measured for the subsequent compression and release cycle and the flow rate assessment is repeated.

Figure 4:
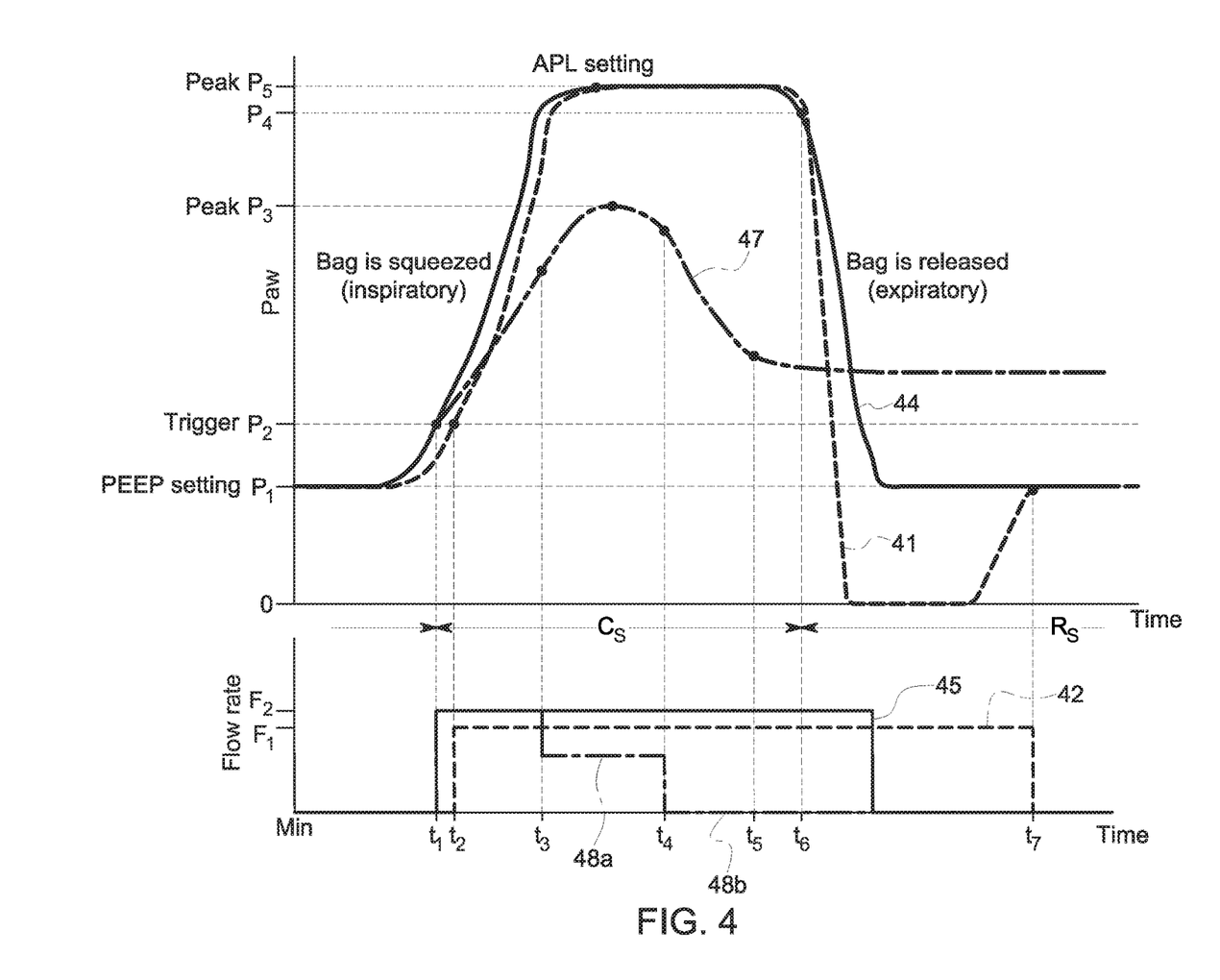
FIG. 4 is graph exemplifying various scenarios of fresh gas flow control during manual ventilation.

In certain embodiments, the initial flow rate and/or a revised flow rate may include adjusting the period during the compression and release cycle for which the fresh gas flow is supplied. In certain embodiments, the initial and/or the adjusted fresh gas flow rate may be a constant flow rate throughout the cycle. In other embodiments, the fresh gas flow may be provided for just a portion of the compression and release cycle. For example, the fresh gas flow may be provided during the compression cycle (i.e., to replace gas being let out through the APL valve), but may be decreased or minimized during the release stroke RS. Referring to FIG. 4, for example, a fresh gas flow rate may be provided according to line 42 in the flow rate portion of the graph, which corresponds with the initial Paw cycle represented at line 41 in the pressure portion of the graph.

The flow rate pattern represented by line 42 provides a minimum flow rate until a threshold pressure is reached upon initiation of the compression stroke, such as a trigger pressure $P_2$. In the examples provided at lines 42 and 48 are steady flow rate values; however, it should be understood that the flow rates 36 and flow rate patterns determined by the manual ventilation control module 22 may be a varied flow throughout the compression and release cycle. In certain embodiments, the trigger pressure exemplified as $P_2$ in FIG. 4, is calculated based on the desired minimum Paw, which may be the PEEP setting. For example, the trigger pressure may be determined as a predetermined pressure amount greater than the PEEP setting, or as a percentage pressure amount greater than the PEEP setting. In the depicted example, the initial Paw cycle represented at line 41 crosses the trigger pressure $P_2$ at time $t_2$. Accordingly, as represented at line 42, the fresh gas flow rate 36 is increased to the flow rate $F_1$ at time $t_2$, which in this example is an initial flow rate and flow pattern. In the depicted example, the initial flow rate $F_1$ is provided until time $t_7$, which is upon detecting that the measured Paw reaches the PEEP setting $P_1$. In other embodiments, the initial flow rate may be provided only during the compression stroke CS, and thus minimized upon detection of the release stroke RS. For example, the initiation of the release stroke may be detected when the measured Paw decreases by a predetermined amount, such as from the peak Paw $P_5$. In the depicted example, the release stroke RS is detected at pressure $P_4$, which is a predetermined pressure amount or pressure percentage below the peak Paw $P_5$ and occurs at time $t_6$. In still other embodiments, the initial flow rate may be maintained for a predetermined amount of time following detection of the trigger pressure $P_2$.

In the depicted embodiment, the initial Paw cycle represented at line 41 increases to a peak pressure $P_5$, which is the APL setting. The measured Paw is maintained at that peak pressure $P_5$ until the breathing bag is released because the APL valve 16 is venting excess gas in order to maintain that peak pressure $P_5$. Then the pressure falls to zero, or atmospheric pressure, during the release stroke RS. Because the fresh gas is continually being added to the system, the pressure slowly climbs back up during the release stroke RS to eventually reach the desired minimum Paw, or PEEP setting $P_1$, at time $t_7$. At that point, the initial flow rate of fresh gas is turned off or minimized.

The manual ventilation control module 22 adjusts the fresh gas flow rate 36 and/or period of time that the flow rate is provided in order to increase the measured minimum Paw toward the PEEP setting for the next compression and release cycle. For example, the fresh gas flow rate 36 may be increased during the compression cycle in order to better compensate for the gas lost through the APL valve 16. The measured minimum Paw is then compared to the PEEP setting $P_1$ and the flow rate adjusted until the measured minimum Paw is consistently within range of the PEEP setting $P_1$. Line 44 of FIG. 4 depicts such a Paw cycle. In certain embodiments, the manual ventilation control module 22 may determine a Paw pattern representing a consistent Paw cycle associated with a physician's consistent compression and release cycle, and where the amount of fresh gas added into the system is balanced such that the measured minimum Paw consistently hovers around the desired minimum Paw. An exemplary flow pattern of fresh gas associated with that Paw pattern 44 is represented at line 45 on the flow rate portion of the graph, where fresh gas flow rate $F_2$ is initiated at time $t_1$ (when the Paw crosses the trigger pressure $P_2$) and continued until the measured Paw is within range of the PEEP setting $P_1$.

The flow pattern that is associated with the Paw pattern can then be repeated consistently in order to maintain the Paw pattern, so long as the clinician's compression and release cycles remain consistent. For example, the Paw pattern 44 may be determined once the measured minimum Paw remains within the predetermined range of the desired minimum Paw, such as represented at point A in FIG. 3. In certain embodiments, the manual ventilation control module 22 may be configured to require a predetermined number of compression and release cycles, where the measured minimum Paw is maintained within range of the desired minimum Paw, before determining the Paw pattern 44 and corresponding flow pattern 45. Once determined, the measured Paw 30 is continually monitored to make sure that it does not deviate from the Paw pattern 44 by more than a predetermined amount, at which point the flow rate may need to be adjusted away from the flow pattern in order to compensate for the change in the Paw.

Figure 5:
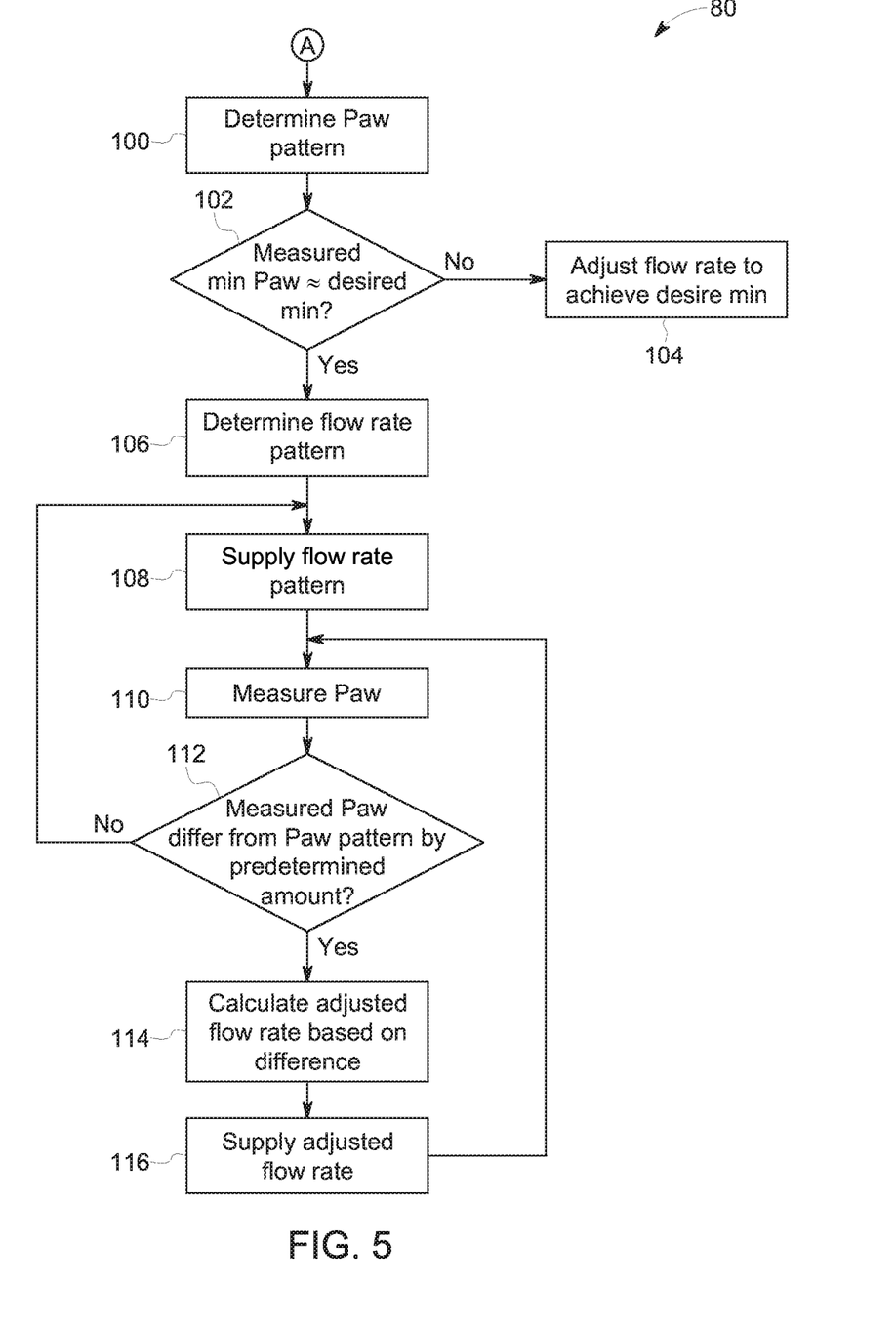
FIGS. 5 and 6A-6B are flow charts depicting steps of another exemplary method, or portion thereof, of controlling fresh gas flow during manual ventilation.

FIG. 5 depicts one embodiment of a method 80 of controlling fresh gas flow during manual ventilation, and specifically a portion of such a method wherein a Paw pattern 44 is determined and the measured Paw 30 is monitored to detect deviation from the Paw pattern 44 and adjust the flow rate accordingly. Instructions are executed at step 100 to determine a Paw pattern 44 based on existing Paw measurements. The Paw pattern 44 is a series of pressure values and/or pressure change rates representing a compression and release cycle. The measured minimum Paw for the Paw pattern is compared to a desired minimum Paw at step 102 to assess whether the Paw pattern represents a gas flow pattern that maintains the desired minimum pressure for the compression and release pattern being performed by the clinician. If the measured minimum Paw is not within a predetermined range of the desired minimum Paw, for example, step 104 is executed to adjust the flow rate in order to bring the measured minimum Paw toward the desired minimum Paw. Once a Paw pattern is identified that consistently reverts to the desired minimum Paw in the release stroke RS, a flow rate pattern is determined at step 106. For example, the flow rate pattern 45 may be the previously-applied pattern, permitting maintenance of the desired Paw cycle represented at line 44 of FIG. 4.

The gas supply system is controlled at step 108 to supply the flow rate pattern 45 during a subsequent compression and release cycle. The Paw is measured at step 110, such as sampled at a predetermined sample rate. The measured Paw 30 is compared to the Paw pattern at step 112 to assess consistency. For example, instructions may be executed to determine whether the measured Paw 30 differs from the Paw pattern by more than a predetermine amount. Alternatively or additionally, the manual ventilation control module 22 may comprise instructions comparing the rate of change of the measured Paw 30 to a model rate of change of the Paw pattern 44. If no significant change is detected, the method returns to step 108 and continues to supply the flow rate pattern and monitor the Paw throughout the compression and release cycle to make sure that the measured Paw is following the Paw pattern. If the measured Paw deviates from the Paw pattern by more than the predetermined amount, then an adjusted flow rate is calculated at step 114. For example, the adjusted flow rate may be calculated based on the difference between the measured Paw 30 and a corresponding portion of the Paw pattern 44. For instance, if the measured Paw deviates from the Paw pattern by just slightly more than the predetermined amount, then a minor adjustment may be made to decrease the flow rate slightly. On the other hand, if the measured Paw differs significantly from the Paw pattern, then the flow rate may be significantly decreased, or even minimized. The gas supply system is controlled to supply the adjusted fresh gas flow rate 36 at step 116.

The manual ventilation control module 22 returns to step 110 to re-measure the Paw and compare it to the Paw pattern. Once the measured Paw 30 is back on track with the Paw pattern 44, the system may revert to utilizing the flow rate pattern 45 to control the fresh gas flow rate 36. In certain embodiments, the manual ventilation control module 22 may include logic that, once a deviation is detected, assesses whether the Paw pattern is still applicable or if a new Paw pattern should be established.

FIG. 4 depicts an exemplary scenario where the measured Paw 30 differs from the Paw pattern 44. Line 47 depicts a measured Paw cycle where the breathing bag 10 was insufficiently compressed by the clinician. Thus, the peak Paw $P_3$ for that particular Paw cycle is significantly below the peak Paw $P_5$ of the Paw pattern 44. Since the peak Paw $P_3$ does not reach the APL setting, gas is not released out of the system. The flow rate line 48 represents an exemplary flow rate sequence that might be executed by the system 1 in such a scenario. The Paw cycle represented at line 47 starts out following the Paw pattern represented at line 44. Accordingly, the flow pattern represented at line 45 is initially followed, which increases the fresh gas flow rate at time $t_1$ when the Paw crosses the trigger pressure $P_2$. However, the measured Paw of line 47 quickly begins to deviate from the Paw pattern of line 44. The Paw pattern of line 47 differs from the Paw pattern by a predetermined amount at time $t_3$. In certain examples, the threshold for determining a material difference between the measured Paw 30 and the Paw pattern may further require detection of the predetermined difference for a minimum number of Paw measurements 30, thereby reducing the errant effects of noise.

The manual ventilation control module 22 calculates an adjusted flow rate based on the deviation, and applies that adjusted flow rate, which is represented at line 48a. The initial reduction in fresh gas flow rate is an attempt to avoid adding too much gas to the system. At time $t_4$, the manual ventilation module 22 detects the initiation of the release cycle RS, such as by detecting that the measured Paw has decreased by a threshold amount. Thus, the fresh gas flow rate is adjusted again to account for the fact that no gas will be released through the APL valve during that compression and release cycle. The fresh gas flow rate is minimized, represented at line 48b, and remains minimized through times $t_5$, $t_6$, and $t_7$ because the minimum measured Paw never reaches the PEEP setting $P_2$. At time $t_5$, for example, the Paw cycle is leveling out toward a minimum measured Paw value that is well above the PEEP setting $P_2$. The manual ventilation control module 22 may then determine that the system is over pressurized, and wait until the measured Paw 30 decreases to at or below the PEEP setting $P_1$ (which may be accomplished, for example, by the clinician compressing the breathing bag 10 past the APL valve setting). At that point, the manual ventilation module 22 may then refine the fresh gas flow rate until the right balance is reached where the measured minimum Paw again equals the desired minimum Paw.

Figure 6A:
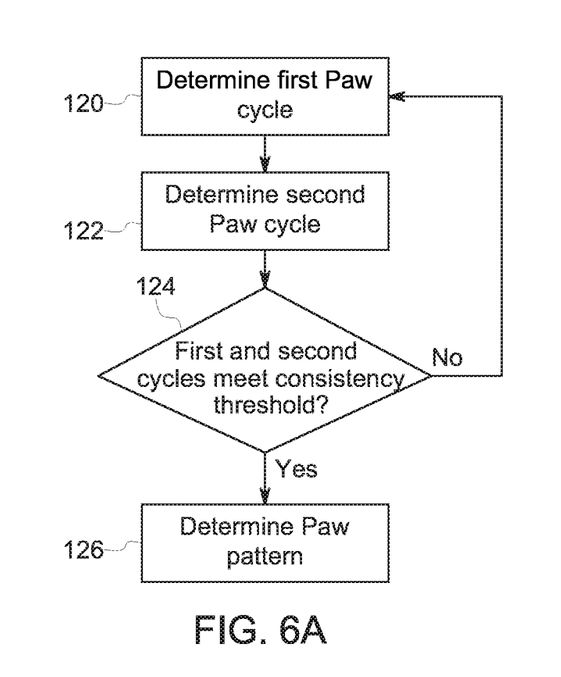
Figure 6B:
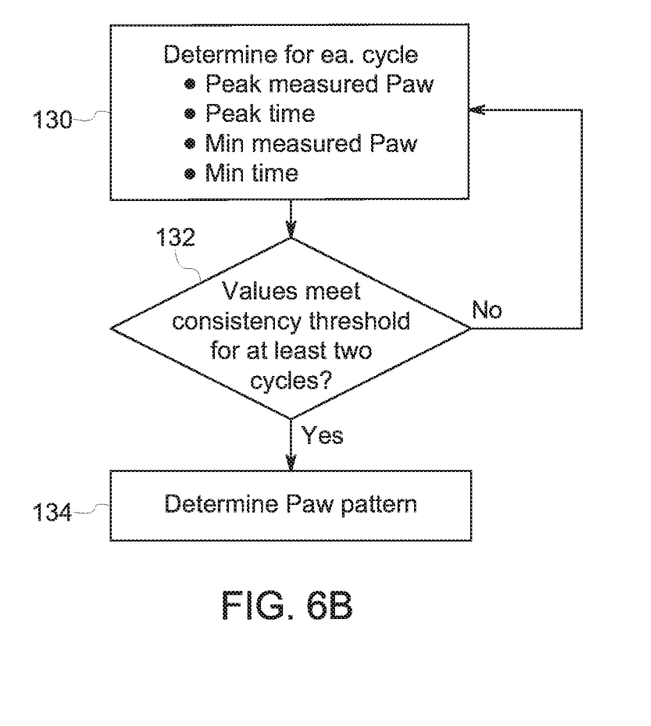

FIGS. 6A and 6B depict exemplary methods for determining a Paw pattern. In the first example, a first Paw cycle is measured at step 120 and a second Paw cycle is measured at step 122. Step 124 is executed to determine whether the first and second Paw cycles are within a predetermined range of one another, such as whether the values through the compression and release strokes are aligned and do not deviate by more than the predetermined range. In certain embodiments, the Paw cycles may be filtered to remove noise prior to making the comparison. If the first and second Paw cycles are approximately equal, then the Paw pattern is determined at step 126. For example, the Paw pattern may be an average of the first and second Paw cycles, or may be just a selected one of the first or second Paw cycles.

FIG. 6B illustrates other exemplary steps that may be executed to determine a Paw pattern. A peak measured Paw and the time of the peak measured Paw, as well as the minimum measured Paw and the time of the minimum measured Paw, are determined for each of two or more compression and release cycles at step 130. Step 132 is executed to determine whether those values meet a consistency threshold for at least two cycles. If so, then the Paw pattern is determined at step 134 based on at least the aforementioned cycle values.

Furthermore, the Paw pattern—whether determined by the method depicted in FIG. 6A, the method depicted in FIG. 6B, or a combination of the two—may further include additional information, such as a derivative of the Paw pattern, or a rate of change pattern during the compression and release cycle. Such information may then be used to assess whether the measured Paw is consistent with the Paw pattern, by comparing the rate of change of the measured Paw to a corresponding portion of the rate of change of the Paw pattern.

FIG. 2 is a schematic system diagram of an exemplary fresh gas controller 20 having a manual ventilation control module 22 executable to determine the fresh gas flow rate 36 based on the measured Paw 30. The fresh gas controller 20 is generally a computing system that includes a processing system 206, storage system 204, software 202, and a communication interface 208. The processing system 206 loads and executes software 202 from the storage system 204, including the manual ventilation control module 22, which is an application within the software 202. The software module 22 includes computer-readable instructions that, when executed by the fresh gas controller 20 (including the processing system 206), direct the processing system 206 to operate as described herein in further detail.

The processing system 206 includes the processor 21, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or subsystems that cooperate in executing program instructions.

Although the fresh gas controller 20 as depicted in FIG. 2 includes one software 202 encapsulating one manual ventilation control module 22, it should be understood that one or more software elements having one or more modules may provide the same operation. Similarly, while description as provided herein refers to a fresh gas controller 20 and a processing system 206, it is to be recognized that implementations of such systems can be performed using one or more processors, which may be communicatively connected, and such implementations are considered to be within the scope of the description.

The storage system 204 may comprise any storage media, or group of storage media, readable by processing system 206 and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or subsystems. Storage system 204 may further include additional elements, such as a controller capable of communicating with the processing system 206.

Examples of storage media include random access memory, read only memory, optical discs, flash memory, virtual memory, non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the fresh gas controller 20 and external devices, such as the pressure sensor 14 and the gas supply system 18, in order to carry out the functions described herein.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A method of controlling fresh gas flow during manual ventilation by a clinician, the method comprising:
    measuring patient airway pressure (Paw) of a patient throughout a compression and release cycle of a breathing bag by the clinician, wherein the Paw is measured with a pressure sensor in a breathing circuit ventilating the patient;
    determining a measured minimum Paw during a release stroke of the compression and release cycle;
    determining a difference between the measured minimum Paw and a desired minimum Paw;
    calculating a fresh gas flow rate of fresh gas into the breathing circuit based on the Paw and the difference between the measured minimum Paw and the desired minimum Paw; and
    controlling a gas supply system to supply fresh gas at the fresh gas flow rate for at least a portion of the compression and release cycle.

2. The method of claim 1, further comprising:
    determining a trigger pressure based on the desired minimum Paw; and
    during a compression stroke of the compression and release cycle, detecting that the Paw exceeds the trigger pressure prior to supplying the fresh gas at the fresh gas flow rate.

3. The method of claim 2, further comprising receiving a positive end expiratory pressure (PEEP) setting and utilizing the PEEP setting as the desired minimum Paw.

4. The method of claim 3, wherein the trigger pressure is one of a predetermined pressure amount greater than the PEEP setting and a percentage pressure amount greater than the PEEP setting.

5. The method of claim 3, further comprising:
    if the measured minimum Paw is within a predetermined range of the PEEP setting, supplying the fresh gas flow rate during a subsequent compression stroke;
    if the measured minimum Paw is less than the predetermined range of the PEEP setting, increasing the fresh gas flow rate during the subsequent compression stroke; and
    if the measured minimum Paw is greater than the predetermined range of the PEEP setting, immediately minimizing the fresh gas flow rate.

6. The method of claim 1, further comprising decreasing the fresh gas flow rate upon detecting the initiation of the release stroke.

7. The method of claim 6, wherein the initiation of the release stroke is detected as a threshold decrease in the measured Paw.

8. The method of claim 1, further comprising:
    determining a rate of change of the Paw during the compression and release cycle;
    wherein the fresh gas flow rate is determined based further on the rate of change of the Paw.

9. The method of claim 1, further comprising:
    determining a Paw pattern based on the measured Paw over two or more compression and release cycles;

determining a flow rate pattern for delivery of the fresh gas into the breathing circuit based on the Paw pattern; and controlling the gas supply system to supply fresh gas into the breathing circuit over a subsequent compression and release cycle based on the flow rate pattern.

10. The method of claim 9, further comprising:

detecting that a Paw measured during the subsequent compression and release cycle differs from the Paw pattern by at least a predetermined amount;

calculating an adjusted fresh gas flow rate based on the difference between the measured Paw and the Paw pattern; and controlling the gas supply system to supply the adjusted fresh gas flow rate.

11. The method of claim 10, wherein the step of detecting that the Paw measured during the subsequent compression and release cycle differs from the Paw pattern includes detecting that a rate of change of the measured Paw differs by more than a predetermined amount from a rate of change of a corresponding portion of the Paw pattern.

12. The method of claim 9, further comprising:

determining a first Paw cycle over a first compression and release cycle, and determining at least a second Paw cycle over a second compression and release cycle; and wherein the Paw pattern is determined based on at least the first Paw cycle and the second Paw cycle.

13. The method of claim 12, further comprising determining that the first Paw cycle and at least the second Paw cycle differ by less than a predetermined amount prior to determining the Paw pattern.

14. The method of claim 9, further comprising:

determining a peak measured Paw, a peak time where the peak measured Paw occurs, and a min time where the minimum measured Paw occurs; and wherein the Paw pattern is determined based on the peak measured Paw, the peak time, the minimum measured Paw, and the min time over the two or more compression and release cycles.

15. A manual patient ventilation system comprising:

a breathing bag manually compressed by a clinician to ventilate a patient via a breathing circuit;

a gas supply system supplying a fresh gas to the breathing circuit;

a pressure sensor measuring a patient airway pressure (Paw) throughout a compression and release cycle of the breathing bag by the clinician;

a fresh gas controller configured to:

receive the Paw measurements;

determine a measured minimum Paw during a release stroke of the compression and release cycle;

determine a difference between the measured minimum Paw and a desired minimum Paw;

calculate a fresh gas flow rate of fresh gas into the breathing circuit based on the Paw and the difference between the measured minimum Paw and the desired minimum Paw; and control the gas supply system to supply the fresh gas into the breathing circuit at the fresh gas flow rate for at least a portion of the compression and release cycle.

16. The system of claim 15, wherein the desired minimum Paw is a positive expiratory pressure (PEEP) setting.

17. The system of claim 16, wherein the fresh gas controller is further configured to:

if the measured minimum Paw is within a predetermined range of the PEEP setting, supply the fresh gas flow rate supplied in a last compression stroke during a subsequent compression stroke;

if the measured minimum Paw is less than the predetermined range of the PEEP setting, increase the fresh gas flow rate during the subsequent compression stroke compared to the fresh gas flow rate supplied in the last compression stroke; and if the measured minimum Paw is greater than the predetermined range of the PEEP setting, immediately minimize the fresh gas flow rate.

18. A manual patient ventilation system comprising:

a breathing bag manually compressed by a clinician to ventilate a patient via a breathing circuit;

a gas supply system supplying a fresh gas to the breathing circuit at a fresh gas flow rate;

a pressure sensor measuring a patient airway pressure (Paw) throughout compression and release cycles of the breathing bag by the clinician;

a fresh gas controller configured to:

receive the Paw measurements;

determine a Paw pattern based on the measured Paw over two or more compression and release cycles;

determine a flow rate pattern for delivery of the fresh gas into the breathing circuit based on the Paw pattern; and control the gas supply system to supply fresh gas into the breathing circuit over a subsequent compression and release cycle based on the flow rate pattern.

19. The system of claim 18, wherein the fresh gas controller is further configured to:

detect that the Paw measured during the subsequent pressure and release cycle differs from the Paw pattern;

calculate an adjusted fresh gas flow rate based on the difference between the measured Paw and the Paw pattern;

control the gas supply system to supply the adjusted fresh gas flow rate.

\* \* \* \* \*